United States Patent
Overett et al.

(10) Patent No.: US 9,499,456 B2
(45) Date of Patent: Nov. 22, 2016

(54) TETRAMERISATION OF ETHYLENE

(71) Applicant: Sasol Technology (Proprietary) Limited, Rosebank (ZA)

(72) Inventors: Matthew James Overett, Johannesburg (ZA); Elzet Grobler, Johannesburg (ZA); Stephen John Evans, Roodepoort (ZA); Kevin Blann, Johannesburg (ZA)

(73) Assignee: SASOL TECHNOLOGY (PROPRIETARY) LIMITED, Rosebank (ZA)

( * ) Notice: Subject to any disclaimer, the term of this patent is extended or adjusted under 35 U.S.C. 154(b) by 88 days.

(21) Appl. No.: 14/399,098

(22) PCT Filed: May 8, 2013

(86) PCT No.: PCT/IB2013/053691
§ 371 (c)(1),
(2) Date: Nov. 5, 2014

(87) PCT Pub. No.: WO2013/168102
PCT Pub. Date: Nov. 14, 2013

(65) Prior Publication Data
US 2015/0080629 A1 Mar. 19, 2015

Related U.S. Application Data

(60) Provisional application No. 61/644,744, filed on May 9, 2012.

(51) Int. Cl.
*C07C 2/36* (2006.01)

(52) U.S. Cl.
CPC .............. *C07C 2/36* (2013.01); *C07C 2531/14* (2013.01); *C07C 2531/24* (2013.01); *C07C 2531/34* (2013.01)

(58) Field of Classification Search
CPC ....... C07C 2/36; C07C 11/107; C07C 11/02; C07C 2531/14; C07C 2531/34; C07C 2531/24

See application file for complete search history.

(56) References Cited

U.S. PATENT DOCUMENTS

| | | | |
|---|---|---|---|
| 6,555,631 B1 † | 4/2003 | Wang | |
| 6,586,550 B2 † | 7/2003 | Cotts | |
| 7,829,749 B2 † | 11/2010 | Gao | |
| 7,994,363 B2 † | 8/2011 | Gao | |
| 2006/0293546 A1 † | 12/2006 | Nabika | |
| 2011/0257350 A1 * | 10/2011 | Jaber et al. ............. C08F 10/00 526/145 |

FOREIGN PATENT DOCUMENTS

| | | | |
|---|---|---|---|
| WO | 2004/056478 A1 † | 7/2004 | |
| WO | 2004/056480 A1 † | 7/2004 | |
| WO | WO 2011/130822 A1 | 10/2011 | |
| WO | WO 2011/140629 A1 | 11/2011 | |

OTHER PUBLICATIONS

International Search Report from the European Patent Office for International Application No. PCT/IB2013/053691 mailed Sep. 19, 2013.
Written Opinion from the European Patent Office for International Application No. PCT/IB2013/053591 mailed Apr. 25, 2014.
Hoffmann Eitle, Notice of Opposition to EP 2 328 905, Oct. 20, 2014.†

\* cited by examiner
† cited by third party

*Primary Examiner* — Nathan M Nutter
(74) *Attorney, Agent, or Firm* — Finnegan Henderson Farabow Garrett & Dunner LLP

(57) ABSTRACT

A process for the tetramerisation of ethylene under solution phase conditions is carried out in the presence of an activated catalyst at a temperature above 80° C. and up to a temperature of about 115° C. The activated catalyst is provided by combining a source of chromium, a diphosphine ligating compound and optionally a catalyst activator or combination of catalyst activators. The process forms at least 30% 1-octene and a polyethylene co-product that, together with any other reaction products, remains substantially dissolved in the liquid phase. The polyethylene co-product has a weight average molecular weight (Mw) of less than 200 000 g/mol, a number average molecular weight (Mn) of less than 3 000 g/mol, and a melt flow index of more than 20 g/10 minutes.

18 Claims, No Drawings

TETRAMERISATION OF ETHYLENE

TECHNICAL FIELD

This invention relates to the tetramerisation of ethylene, in particular in the presence of an activated tetramerisation catalyst under solution phase conditions.

BACKGROUND OF THE INVENTION

It is known that chromium-based catalyst systems with diphosphine ligands catalyse the selective conversion of ethylene to 1-hexene and/or 1-octene, depending on the reaction conditions and choice of ligand structure. In particular, the nature and position of any substituents on the aryl rings connected to the phosphines are crucial influences on the selectivity towards tetramerisation of ethylene. By tetramerisation it is meant that at least 30% 1-octene is produced in the process.

Non-limiting examples of selective ethylene tetramerisation catalyst systems include the ubiquitous Cr/bis(phosphino)amine (i.e. 'PNP') systems, particularly of the type $(Ar^1)(Ar^2)PN(R)P(Ar^3)(Ar^4)$, where $Ar^1$ to $Ar^4$ are aryl groups such as phenyl and R is a hydrocarbyl or a heterohydrocarbyl group, beginning with PNP ligands containing no substituents on the phenyl rings bonded to the P-atoms (e.g. as described in WO 2004/056479) and those with m- or p-methoxy groups on the phenyl rings (e.g. as described in WO 2004/056480). In addition to this, PNP systems containing o-fluoro groups on the phenyl rings are described in US 2008/0242811 and US 2010/008177, and PNP systems bearing pendant donor atoms on the nitrogen linker are described in WO 2007/088329. Multi-site PNP ligands are discussed in US 2008/0027188. In addition to the Cr/PNP systems, chromium systems bearing N,N-bidentate ligands (e.g. as described in US 2006/0247399) can be used. PNP ligands with alkylamine or phosphinoamine groups bonded to one of the PNP phosphines (i.e. 'PNPNH' and 'PNPNP' ligands) are described in WO 2009/006979. Finally, carbon bridged diphosphine (i.e. 'PCCP' ligands) are described in WO 2008/088178 and WO 2009/022770.

A serious drawback for tetramerisation catalysts generally is the low catalyst activity when operated at elevated temperatures, especially above 80° C. This may be explained in some cases by catalyst deactivation at elevated temperatures as described in Applied Catalysis A: General 306 (2006) 184-191.

In a recent review article describing catalyst systems for ethylene tetramerisation, van Leeuwen at al (Coordination Chemistry Reviews, 255, (2011), 1499-1517) have discussed the problems associated with elevated reaction temperatures. They state that: "In general the selective ethylene tetramerisation experiments are performed in the temperature range 40-60° C. Various studies on both semi-batch and continuous mini plant have shown a strong dependency of the reaction temperature on the activity and selectivity of the Cr(III)/Ph$_2$N(R)PPh$_2$/MAO catalytic system. High reaction temperatures (>60° C.) significantly reduced the catalyst productivity as compared to reactions performed at lower temperature under the same ethylene pressure. Consequently catalyst decomposition with increasing temperature is probably the main reason for lower productivities at high temperatures.

When carrying out a process for tetramerisation of ethylene, the aim is to choose a catalyst system and adjust process conditions in order to produce the maximum amount of 1-octene, as opposed to trimerisation processes where catalysts and process conditions are adjusted to produce the maximum amount of 1-hexene. 1-Hexene is also typically co-produced in a tetramerisation process and it is well known in the art of the invention that higher temperatures shift the selectivity from 1-octene towards 1-hexene. This is a further issue to consider when operating a tetramerisation process at higher temperatures.

Furthermore, the formation of a high molecular weight polymer co-product by the Cr-based ethylene tetramerisation catalyst may present a major technical challenge when commercialising an ethylene tetramerisation process as polymer fouling reduces plant run time and necessitates shut-downs due to blockages and difficult temperature control. When running tetramerisation processes at reaction temperatures in the range of 40 to 80° C., the polymer precipitates out of solution in the reactor, which brings risk to the process due to the possibility of reactor or downstream equipment fouling.

Running a tetramerisation process at process conditions where the polymer co-product remains predominantly dissolved in the liquid reaction medium in the reactor (i.e. a solution phase process) would substantially reduce the possibility of reactor or downstream fouling. For example, in the field of polymerisation, solution-phase polyethylene processes are used by Dow Chemicals (Dowlex™ process) and Nova Chemicals (Sclairtech™ and Advanced Sclairtech™ processes) to produce high value linear low density polyethylene products (*Linear Low Density Polyethylene, Process Economics Program Report* 36E, Susan Bell, August 2008). However these processes run at reaction temperatures of about 150° C. to 300° C., such high temperatures being required to keep the polyethylene product in solution.

SUMMARY OF THE INVENTION

According to one aspect of the invention there is provided a continuous process for the tetramerisation of ethylene, the process including:
(a) providing an activated catalyst comprising:
  i) a source of chromium;
  ii) a ligating compound of the formula $R^1R^2P^1XP^2R^3R^4$ wherein $P^1$ and $P^2$ are phosphorus atoms;
  X is a linking group between $P^1$ and $P^2$, such that any heteroatom on the shortest connecting path between $P^1$ and $P^2$ is either bound to $P^1$ or $P^2$ or adjacent to an atom bound to $P^1$ or $P^2$; and
  $R^1$ to $R^4$ are independently a hydrocarbyl group, an organoheteryl group or a heterohydrocarbyl group; and
  iii) optionally a catalyst activator or combination of catalyst activators; and
(b) contacting ethylene to be tetramerised with the activated catalyst at a reaction temperature of from above 80° C. to about 115° C., thereby to form at least 30% 1-octene and a polyethylene co-product that, together with any other reaction products, remains substantially dissolved in the liquid phase, the polyethylene co-product being characterised as having:
  i) a weight average molecular weight (Mw), as determined by gel permeation chromatography, of less than 200 000 g/mol;
  ii) a number average molecular weight (Mn), as determined by gel permeation chromatography, of less than 3 000 g/mol; and iii) a melt flow index, as determined by ASTM method D1238 at 190° C. and 21.6 kg, of more than 20 g/10 minutes.

In some embodiments of the invention the ethylene is contacted with the activated catalyst at a reaction temperature of from above 85° C. to about 110° C., or from above 85° C. to about 100° C.

In some embodiments of the invention the ethylene is contacted with the activated catalyst at a reaction temperature of from above 90° C. to about 105° C.

In some embodiments of the invention the ethylene is contacted with the activated catalyst at a reaction temperature of from above 80° C. or above 85° C. or above 90° C. to about 115° C. or about 110° C. or about 105° C. or about 100° C.

DETAILED DESCRIPTION OF EMBODIMENTS OF THE INVENTION

The invention relates to a process for the tetramerisation of ethylene under solution phase conditions. The process is carried out in the presence of an activated catalyst at a temperature above 80° C. and up to a temperature of about 115° C. The activated catalyst is provided by combining a source of chromium, a diphosphine ligating compound and optionally a catalyst activator or combination of catalyst activators.

In the specification, the following definitions apply:

A "hydrocarbyl group" as per IUPAC includes a univalent group formed by removing one hydrogen atom from a hydrocarbon;

A "heterohydrocarbyl group" as defined herein is a univalent group formed by removing one hydrogen atom from a carbon atom of a heterohydrocarbon, that is a hydrocarbon compound which includes at least one hetero atom (that is, not being H or C), and which group covalently bonds with one other moiety through the resultant free valency on that carbon atom;

An "organoheteryl group" as per IUPAC includes univalent groups containing carbon, which are thus organic, but which have their free valence at an atom other than carbon;

A "hydrocarbylene group" as per IUPAC includes divalent groups formed by removing two hydrogen atoms from a hydrocarbon, the free valencies of which are not engaged in a double bond;

A "heterohydrocarbylene group" as defined herein is a divalent group formed by removing two hydrogen atoms from either one or two carbon atoms of an organic molecule containing at least one heteroatom, the free valencies of which are not engaged in a double bond;

A "polarising substituent" is a substituent that, when bonded to any one of $R^1$ to $R^4$, creates a permanent electric dipole moment over the bond between the substituent and the substituted moiety.

A "non-polar substituent" is a substituent without a permanent electric dipole moment.

Chromium Source (a)(i):

Any source of chromium that allows the oligomerisation to proceed may be used. The source of chromium may be an inorganic salt, an organic salt, a coordination compound or an organometallic complex.

In some embodiments the source of chromium is selected from the group consisting of chromium trichloride tris-tetrahydrofuran complex, (benzene)tricarbonyl chromium, chromium (III) octanoate, chromium hexacarbonyl, chromium (III) acetylacetonate, chromium (III) naphthenate, chromium (III) 2-ethylhexanoate, chromium (III) acetate, chromium (III) 2,2,6,6-tetramethylheptadionate, and chromium (III) chloride. In some embodiments it is chromium (III) acetylacetonate or chromium (III) 2-ethylhexanoate.

The chromium source may be introduced to the process as a coordination complex of the ligating compound. However, for reasons of cost and commercial operability, in some embodiments the ligating compound and chromium source are added as separate components to the process. Catalyst systems which give good catalyst performance only when an isolable chromium-ligand coordination complex is used therefore suffer a disadvantage to catalyst systems which can be prepared by mixing a chromium source and ligand in the process.

Ligating Compound (a)(ii):

Linking Group X

X is a linking group between $P^1$ and $P^2$, such that any heteroatom on the shortest connecting path between $P^1$ and $P^2$ is either bound to $P^1$ or $P^2$ or adjacent to an atom bound to $P^1$ or $P^2$. Not wishing to be bound by theory, this is to ensure that X is non-coordinating to chromium in the activated catalyst. X may be selected from the group consisting of an organic linking group such as a hydrocarbylene, heterohydrocarbylene; an inorganic linking group comprising either a single- or two-atom linker spacer; and a group comprising dimethylmethylene, ethane-1,2-diyl, ethene-1,2-diyl, propane-1,2-diyl, propane-1,3-diyl, cyclopropane-1,1-diyl, cyclopropane-1,2-diyl, butane-2,3-diyl, cyclobutane-1,2-diyl, cyclopentane-1,2-diyl, cyclohexane-1,2-diyl, cyclohexane-1,1-diyl, 1,2-phenylene, naphthalene-1,8-diyl, phenanthrene-9,10-diyl, phenanthrene-4,5-diyl, 9,10-anthracene-diyl, 1,2-catecholate, 1,2-diarylhydrazine-1,2-diyl (—N(Ar)—N(Ar)— where Ar is an aryl group), 1,2-dialkylhydrazine-1,2-diyl (—N(Alk)-N(Alk)- where Alk is an alkyl or a cycloalkyl group), 1-alkyl-2-arylhydrazine-1,2-diyl (—N(Alk)-N(Ar)— where Alk is an alkyl or a cycloalkyl group and Ar is an aryl group), —N(R')—$X^1$—N(R")— where R' and R" are independently alkyl, cycloalkyl or aryl groups and $X^1$ is a hydrocarbylene group, —B($R^5$)—, —Si($R^5$)$_2$—, —P($R^5$)— and —N($R^5$)— where $R^5$ is hydrogen, a hydrocarbyl group, an organoheteryl group or a heterohydrocarbyl group. Preferably $R^5$ is a hydrocarbyl group or a heterohydrocarbyl group.

In some embodiments X consists of —N($R^6$)—, —N($R^6$)—N($R^7$)—, —C($R^{8a}$)($R^{8b}$)—N($R^6$)— or a hydrocarbylene, where $R^6$ and $R^7$ are independently a hydrocarbyl group, a heterohydrocarbyl group or an organoheteryl group, and $R^{8a}$ and $R^{8b}$ are independently a hydrogen, a hydrocarbyl group, a heterohydrocarbyl group or an organoheteryl group. In some embodiments $R^6$, $R^7$, $R^{8a}$ and $R^{8b}$ may be an alkyl, cycloalkyl, substituted alkyl, substituted cycloalkyl, aryl, substituted aryl, aryloxy, substituted aryloxy, alkoxycarbonyl, carbonyloxy, alkoxy, aminocarbonyl, carbonylamino, dialkylamino, pyrolyl, silyl group or derivative thereof, and aryl substituted with any of these substituents, and $R^{8a}$ and $R^{8b}$ may additionally be hydrogen. In some embodiments $R^6$, $R^7$, $R^{8a}$ and $R^{8b}$ may be an alkyl, cycloalkyl, substituted alkyl, substituted cycloalkyl, aryl, substituted aryl, dialkylamino, silyl group or derivative thereof, and $R^{8a}$ and $R^{8b}$ may additionally be hydrogen. In some embodiments, $R^6$, $R^7$, $R^{8a}$ and $R^{8b}$ consist of hydrocarbyl groups, such as methyl, ethyl, propyl, allyl, isopropyl, cyclopropyl, butyl, tertiary-butyl, sec-butyl, cyclobutyl, pentyl, isopentyl, 1,2-dimethylpropyl (3-methyl-2-butyl), 1,2,2-trimethylpropyl (R/S-3,3-dimethyl-2-butyl), 1-(1-methylcyclopropyl)-ethyl, neopentyl, cyctopentyl, cyclohexyl, hexyl, cycloheptyl, cyclo-octyl, decyl, cyclodecyl, 1,5-dimethylheptyl, 1-methylheptyl, 2-naphthylethyl, 1-naphthylmethyl, adamantylmethyl, 1-adamantyl, 2-adamantyl, 2-isopropylcyclohexyl, 2,6-dimethylcyclohexyl, cyclododecyl, 2-methylcyclohexyl, 3-methylcyclohexyl, 4-methylcyclohexyl, 2-ethylcyclohexyl, 2-isopropylcyclohexyl, 2,6-dimethyl-cyclohexyl, exo-2-norbornanyl, (1,1'-bis(cyclohexyl)-4,4'-methylene), 1,6-hexylene, 1-naphthyl, 2-naphthyl, diphenylmethyl, 1,2-diphenyl-ethyl, phenylethyl, 2-methylphenyl, 3-methylphenyl, 4-methylphenyl, 2,6-dimethyl-phenyl, or a 1,2,3,4-tetrahydronaphthyl, and $R^{8a}$ and $R^{8b}$ may additionally be hydrogen.

In a preferred embodiment X is a hydrocarbylene, $-N(R^5)-$, $-N(R^5)-N(R^6)-$, $-N(R^5)-C(R^7)(R^8)-$, $N(R^5)-X^1-N(R^6)$ where $R^5$ and $R^6$ are independently a hydrocarbyl group, an organoheteryl group or a heterohydrocarbyl group, $R^7$ and $R^8$ are independently a hydrogen, a hydrocarbyl group, an organoheteryl group or a heterohydrocarbyl group, and $X^1$ is a hydrocarbylene group.

In some embodiments, X is $-N(R^9)-$, where $R^9$ is a hydrocarbyl group, a heterohydrocarbyl group or an organoheteryl group. In some embodiments $R^9$ is a hydrocarbyl group or a heterohydrocarbyl group. In some embodiments $R^9$ is an alkyl, cycloalkyl or aryl group. In some embodiments $R^9$ is an alkyl or cycloalkyl group. In some embodiments $R^9$ is an alkyl group of the form $-CH_2R^{10}$, where $R^{10}$ is hydrogen or an alkyl group or a cycloalkyl group. In some embodiments $R^9$ is methyl or a linear alkyl group Nature of the Groups $R^1$-$R^4$ $R^1$ to $R^4$ are independently a hydrocarbyl, an organoheteryl group or a heterohydrocarbyl group. In some embodiments, $R^1$ to $R^4$ are independently a hydrocarbyl or a heterohydrocarbyl group. In some embodiments at least one of $R^1$ to $R^4$ includes an aromatic moiety or a heteroaromatic moiety directly bonded to $P^1$ or $P^2$. In some embodiments $R^1$ to $R^4$ all include aromatic or heteroaromatic moieties directly bonded to $P^1$ or $P^2$. In some embodiments $R^1$ to $R^4$ are optionally substituted phenyl groups. In some embodiments, at least one of $R^1$ to $R^4$ is an ortho-substituted phenyl group In some embodiments, at least one of $R^1$ to $R^4$ is an optionally substituted 2-fluorophenyl group.

In this specification, a substituent with reference to moieties bound to $P^1$ and/or $P^2$ is a moiety (excluding H) that is bound to a linear structure or a cyclic structure bound to $P^1$ and/or $P^2$, but the substituent does not form part of the linear or cyclic structure.

In some embodiments at least one of $R^1$ to $R^4$ is an aromatic moiety of which a ring atom of the aromatic ring structure is bound to either $P^1$ or $P^2$ and which has a polarising substituent bound to a ring atom of the aromatic ring structure adjacent to the ring atom bound to $P^1$ or $P^2$. Examples of suitable polarising substituents include, but are not limited to, methoxy, ethoxy, isopropoxy, $C_3$-$C_{20}$ alkoxy, phenoxy, methoxymethyl, methylthiomethyl, 1,3-oxazolyl, methoxymethoxy, hydroxyl, amino, tosyl, methylsulfanyl, trimethylsiloxy, dimethylamino, sulphate, nitro, halogens or the like. Any polarising substituent on one or more of $R^1$, $R^2$, $R^3$ and $R^4$ may be electron donating or electron withdrawing. In some embodiments, any polarising substituent on one or more of $R^1$, $R^2$, $R^3$ and $R^4$ is electron withdrawing. In some embodiments, the polarising substituent bound to a ring atom of the aromatic ring structure adjacent to the ring atom bound to $P^1$ or $P^2$ is a halogen selected from the group consisting of fluorine, chlorine or bromine, such that one, two, three or four of $R^1$ to $R^4$ are substituted with a halogen at a ring atom of the aromatic ring structure adjacent to the ring atom bound to $P^1$ or $P^2$. In some embodiments the halogen is fluorine.

In some embodiments at least one of $R^1$ to $R^4$ is an aromatic moiety of which a ring atom of the aromatic ring structure is bound to either $P^1$ or $P^2$ and which has a non-polar substituent bound to a ring atom of the aromatic ring structure adjacent to the ring atom bound to $P^1$ or $P^2$. Examples of suitable non-polar substituents include, but are not limited to, methyl, ethyl, ethenyl, propyl, iso-propyl, cyclopropyl, propenyl, propynyl, butyl, sec-butyl, tertiary-butyl, cyclobutyl, butenyl, butynyl, pentyl, isopentyl, neopentyl, cyclopentyl, pentenyl, pentynyl, hexyl, sec-hexyl, cyclohexyl, 2-methylcyclohexyl, 2-ethylcyclohexyl, 2-isopropylcyclohexyl, cyclohexenyl, hexenyl, hexynyl, octyl, cyclo-octyl, cyclo-octenyl, decyl, benzyl, phenyl, tolyl, xylyl, o-methylphenyl, o-ethylphenyl, o-isopropylphenyl, o-t-butylphenyl, cumyl, mesityl, biphenyl, naphthyl, anthracenyl, and the like. In some embodiments, the non-polar substituent is an alkyl or cycloalkyl group such that one, two, three or four of $R^1$ to $R^4$ are substituted with an alkyl or cycloalkyl group at a ring atom of the aromatic ring structure adjacent to the ring atom bound to $P^1$ or $P^2$. In some embodiments the non-polar group is selected from the group consisting of methyl, ethyl and isopropyl. In some embodiments the non-polar group is methyl.

If two or more of $R^1$ to $R^4$ are aromatic moieties with a ring atom of the aromatic ring structure bound to either $P^1$ or $P^2$, in some embodiments not more than two of said aromatic moieties $R^1$ to $R^4$ have a substituent bound to a ring atom of the aromatic ring structure adjacent to the ring atom bound to $P^1$ or $P^2$.

In some embodiments, $R^1$ and $R^2$ are aromatic moieties of which a ring atom of the aromatic ring structure is bound to $P^1$ and which has a substituent bound to a ring atom of the aromatic ring structure adjacent to the ring atom bound to $P^1$, and $R^3$ and $R^4$, if they are aromatic moieties of which a ring atom of the aromatic ring structure is bound to $P^2$, do not have a substituent bound to a ring atom of the aromatic ring structure adjacent to the ring atom bound to $P^2$.

In some embodiments, $R^1$ is an aromatic moiety of which a ring atom of the aromatic ring structure is bound to $P^1$ and which has a substituent bound to a ring atom of the aromatic ring structure adjacent to the ring atom bound to $P^1$, and $R^2$, $R^3$ and $R^4$, if they are aromatic moieties of which a ring atom of the aromatic ring structure is bound to $P^1$ or $P^2$, do not have a substituent bound to a ring atom of the aromatic ring structure adjacent to the ring atom bound to $P^1$ or $P^2$.

Other Considerations

Any one of $R^1$ to $R^4$ may independently be linked to one or more of each other, or to X, to form a cyclic structure.

The ligating compound may also include multiple $R^1R^2P^1XP^2R^3R^4$ units. Non-limiting examples of such ligands include dendrimeric ligands as well as ligands where the individual units are coupled either via one or more of the $R^1$-$R^4$ groups or via the linking group X.

It will be appreciated that a diphosphinoimine compound of the form $R^1R^2P^1-P^2(=NR^9)R^3R^4$ ('P—P=N') is a rearranged isomer of the diphosphinoamine compound $R^1R^2P^1N(R^9)P^2R^3R^4$ ('P—N—P') claimed in the present invention, as shown by Dyson et al in Inorganica Chimica Acta 359 (2006) 2635-2643. Regardless of the structural formulation of the ligating compound in its pure and isolated form, its use will fall under the present invention if it exists in the 'P—N—P' form when used in a tetramerisation process.

In some embodiments the ligating compound may be one of:

(phenyl)$_2$PN(methyl)P(phenyl)$_2$; (phenyl)$_2$PN(ethyl)P(phenyl)$_2$; (phenyl)$_2$PN(propyl)P(phenyl)$_2$; (phenyl)$_2$PN (butyl)P(phenyl)$_2$; (phenyl)$_2$PN(pentyl)P(phenyl)$_2$; (phenyl)$_2$PN(hexyl)P(phenyl)$_2$; (phenyl)$_2$PN(heptyl)P(phenyl)$_2$; (phenyl)$_2$PN(octyl)P(phenyl)$_2$; (phenyl)$_2$PN(nonyl)P(phenyl)$_2$; (phenyl)$_2$PN(decyl)P(phenyl)$_2$; (phenyl)$_2$PN(cyclopropyl)P(phenyl)$_2$; (phenyl)$_2$PN(cyclobutyl)P(phenyl)$_2$; (phenyl)$_2$PN(cyclopentyl)P(phenyl)$_2$; (phenyl)$_2$PN(cyclohexyl)P(phenyl)$_2$; (phenyl)$_2$PN(cycloheptyl)P(phenyl)$_2$; (phenyl)$_2$PN(cycloactyl)P(phenyl)$_2$; (phenyl)$_2$PN(cyclodecyl)P(phenyl)$_2$; (phenyl)$_2$PN(cyclododecyl)P(phenyl)$_2$; (phenyl)$_2$PN(isopropyl)P(phenyl)$_2$; (phenyl)$_2$PN(isobutyl)P(phenyl)$_2$; (phenyl)$_2$PN(secbutyl)P(phenyl)$_2$; (phenyl)$_2$PN(tertiarybutyl)P(phenyl)$_2$; (phenyl)$_2$PN(neopentyl)P(phenyl)$_2$; (phenyl)$_2$PN(1,2-dimethyl-propyl)P(phenyl)$_2$; (phenyl)$_2$PN(allyl)P(phenyl)$_2$; (phenyl)$_2$PN(methylheptyl)P(phenyl)$_2$; (phenyl)$_2$PN(1,5-dimethylheptyl)P(phenyl)$_2$; (phenyl)$_2$PN(2-ethylhexyl)P(phenyl)$_2$; (phenyl)$_2$PN(adamantyl)P(phenyl)$_2$; (phenyl)$_2$PN(adamantylmethyl)P(phenyl)$_2$; (phenyl)$_2$PN(3-trimethoxysilane-propyl)P(phenyl)$_2$; (phenyl)$_2$PN(indanyl)P(phenyl)$_2$; (phenyl)$_2$PN(cyclohexylethyl)P(phenyl)$_2$; (phenyl)$_2$PN(2-methylcyclohexyl)P(phenyl)$_2$; (phenyl)$_2$PN(cyclohexanemethyl)P(phenyl)$_2$; (phenyl)$_2$PN(benzyl)P(phenyl)$_2$; (phenyl)$_2$PN(phenyl)P(phenyl)$_2$; (phenyl)$_2$PN((4-methoxy)-phenyl)P(phenyl)$_2$; (phenyl)$_2$PN((3-methoxy)phenyl)P(phenyl)$_2$; (phenyl)$_2$PN((2-methoxy)phenyl)P(phenyl)$_2$; (phenyl)$_2$PN((4-t-butyl)-phenyl)P(phenyl)$_2$; (phenyl)$_2$PN((4-nitro)-phenyl)P(phenyl)$_2$; (phenyl)$_2$PN(1-naphthyl)P(phenyl)$_2$; (phenyl)$_2$ PN(2-naphthyl)P(phenyl)$_2$; (phenyl)$_2$PN(4-pyridyl)P(phenyl)$_2$; (phenyl)$_2$PN(3-(N-morpholine)-propyl)P(phenyl)$_2$; (phenyl)$_2$PN(2-naphtyl-ethyl)P(phenyl)$_2$; (phenyl)$_2$PN(1-naphtylmethyl)P(phenyl)$_2$; (phenyl)$_2$PN(diphenylmethyl)P(phenyl)$_2$; (phenyl)$_2$PN(1,2-diphenyl-ethyl)P(phenyl)$_2$; (phenyl)$_2$PN(phenylethyl)P(phenyl)$_2$; (phenyl)$_2$PN((2-methyl)phenyl)P(phenyl)$_2$; (phenyl)$_2$PN((3-methyl)phenyl)P(phenyl)$_2$; (phenyl)$_2$PN((4-methyl)phenyl)P(phenyl)$_2$; (phenyl)$_2$PN((2,6-dimethyl)phenyl)P(phenyl)$_2$; (phenyl)$_2$PN((2-ethyl)-phenyl)P(phenyl)$_2$; (phenyl)$_2$PN(1,2,3,4-Tetrahydronaphthyl)P(phenyl)$_2$; (phenyl)$_2$PN((2-methyl)cyclohexyl)P(phenyl)$_2$; (phenyl)$_2$PN((3-methyl)cyclohexyl)P(phenyl)$_2$; (phenyl)$_2$PN((4-methyl)cyclohexyl)P(phenyl)$_2$; (phenyl)$_2$PN((2-ethyl)cyclohexyl)P(phenyl)$_2$; (phenyl)$_2$PN((2-isopropyl)cyclohexyl)P(phenyl)$_2$; (phenyl)$_2$PN((2,6-imethyl)cyclohexyl)P(phenyl)$_2$; (phenyl)$_2$PN(exo-2-norbornanyl)P(phenyl)$_2$; (phenyl)$_2$PN(isopinocampheyl)P(phenyl)$_2$; (phenyl)$_2$PN(dimethylamino)P(phenyl)$_2$; (phenyl)$_2$PN(phthalimido)P(phenyl)$_2$; (phenyl)$_2$PN(pyrrolyl)P(phenyl)$_2$; (phenyl)$_2$PN(trimethylsiyl)P(phenyl)$_2$; (phenyl)$_2$PN(dimethyltertiarybutylsityl)P(phenyl)$_2$; [(phenyl)$_2$P]$_2$N(1,1'-bis(cyclohexyl)-4,4'-methylene))N[P(phenyl)$_2$]$_2$; ([(phenyl)$_2$ P]$_2$N(1,6-hexylene-)N[P(phenyl)$_2$]$_2$]; (2,2',2"-triethylamino)[N[P(phenyl)$_2$]$_2$]$_3$; (4-biphenyl)PN(methyl)P(4-biphenyl); (2-naphthyl)$_2$PN(methyl)P(2-naphthyl)$_2$; (4-methylphenyl)$_2$PN(methyl)P(4-methylphenyl)$_2$; (3-methylphenyl)$_2$PN(methyl)P(3-methylphenyl)$_2$; (2-naphthyl)$_2$PN(methyl)P(phenyl)$_2$; (2-naphthyl)(phenyl)PN(methyl)P(2-naphthyl)(phenyl); (2-naphthyl)$_2$PN(methyl)P(2-naphthyl)(phenyl); (2-naphthyl)(phenyl)PN(methyl)P(phenyl)$_2$; (ethyl)$_2$PN(methyl)P(ethyl)$_2$; (ethyl)$_2$PN(isopropyl)P(ethyl)$_2$; (ethyl)$_2$PN(tertiarybutyl)P(ethyl)$_2$; (methyl)$_2$PN(isopropyl)P(methyl)$_2$; (isopropyl)$_2$PN(methyl)P(isopropyl)$_2$; (ethyl)$_2$PN(isopropyl)P(ethyl)(phenyl); (ethyl)(phenyl)PN(isopropyl)P(ethyl)(phenyl); (ethyl)$_2$PN(isopropyl)P(phenyl)$_2$; (ethyl)(phenyl)PN(isopropyl)P(phenyl)$_2$; (diphenylphosphonite)N(isopropyl)(diphenylphosphonite); (diphenylphosphonite)N(isopropyl)(diphenylphosphonite); (phenyl)$_2$PN(methyl)N(methyl)P(phenyl)$_2$; (phenyl)$_2$PN(ethyl)N(ethyl)P(phenyl)$_2$; (phenyl)$_2$PN(phenyl)N(phenyl)P(phenyl)$_2$; (phenyl)$_2$PN(isopropyl)N(isopropyl)P(phenyl)$_2$; (phenyl)$_2$PN(isopropyl)N(methyl)P(phenyl)$_2$; (phenyl)$_2$PN(isopropyl)N(methyl)P(phenyl)$_2$; (4-methylphenyl)$_2$P—N(CH$_3$)N(CH$_3$)—P(4-methylphenyl)$_2$; (3-methylphenyl)$_2$P—N(CH$_3$)N(CH$_3$)—P(3-methylphenyl)$_2$; (ethyl)$_2$P—N(CH$_3$)N(CH$_3$)—P(ethyl)$_2$; (methyl)$_2$P—N(CH$_3$)N(CH$_3$)—P(methyl)$_2$; (isopropyl)$_2$P—N(CH$_3$)N(CH$_3$)—P(isopropyl)$_2$; (ethyl)$_2$P—N(CH$_3$)N(CH$_3$)—P(ethyl)(phenyl); (ethyl)(phenyl)P—N(CH$_3$)N(CH$_3$)—P(ethyl)(phenyl); (ethyl)$_2$P—N(CH$_3$)N(CH$_3$)—P(phenyl)$_2$; (ethyl)(phenyl)P—N(CH$_3$)N(CH$_3$)—P(phenyl)$_2$; (4-biphenyl)$_2$P—N(CH$_3$)N(CH$_3$)—P(4-biphenyl)$_2$; (phenyl)$_2$P-1,8-naphthyl-P(phenyl)$_2$; (phenyl)$_2$P-9,10-phenanthrene-P(phenyl)$_2$; (phenyl)$_2$P-4,5-phenanthrene-P(phenyl)$_2$; (phenyl)$_2$P—C(CH$_3$)$_2$—P(phenyl)$_2$; (phenyl)$_2$P—C(CH$_2$)$_2$—P(phenyl)$_2$; (phenyl)$_2$P-1,2-benzene-P(phenyl)$_2$; (4-methylphenyl)$_2$P-1,2-benzene-P(4-methylphenyl)$_2$; (3-methylphenyl)$_2$P-1,2-benzene-P(3-methylphenyl)$_2$; (methyl)$_2$P-1,2-benzene-P(methyl)$_2$; (isopropyl)$_2$P-1,2-benzene-P(isopropyl)$_2$; (ethyl)$_2$P-1,2-benzene-P(ethyl)(phenyl); (ethyl)(phenyl)P-1,2-benzene-P(ethyl)(phenyl); (ethyl)$_2$P-1,2-benzene-P(phenyl)$_2$; (ethyl)(phenyl)P-1,2-benzene-P(phenyl)$_2$; (2-naphthyl)$_2$P-1,2-benzene-P(2-naphthyl)$_2$; (4-biphenyl)$_2$P-1,2-benzene-P(4-biphenyl)$_2$; (phenyl)$_2$P—CH2CH2-P(phenyl)$_2$; R,R-(phenyl)$_2$P—CH(Me)CH(Me)-P(phenyl)$_2$; S,S-(phenyl)$_2$P—CH(Me)CH(Me)-P(phenyl)$_2$; meso-(phenyl)$_2$P—CH(Me)CH(Me)-P(phenyl)$_2$; (4-methylphenyl)$_2$P—CH$_2$CH$_2$—P(4-methylphenyl)$_2$; (3-methylphenyl)$_2$P—CH$_2$CH$_2$—P(3-methylphenyl)$_2$; (4-methylphenyl)$_2$P—CH$_2$CH$_2$—P(4-methylphenyl)(phenyl); (4-methylphenyl)(phenyl)P—CH$_2$CH$_2$—P(4-methylphenyl)(phenyl); (4-methylphenyl)$_2$P—CH$_2$CH$_2$—P(phenyl)$_2$; (4-methylphenyl)(phenyl)P—CH$_2$CH$_2$—P(phenyl)$_2$; (methyl)$_2$P—CH$_2$CH$_2$—P(methyl)$_2$; (isopropyl)$_2$P—CH2CH$_2$—P(isopropyl)$_2$; (ethyl)$_2$P—CH$_2$CH$_2$—P(ethyl)(phenyl); (ethyl)(phenyl)P—CH2CH$_2$—P(ethyl)(phenyl); (ethyl)$_2$P—CH$_2$CH$_2$—P(phenyl)$_2$; (ethyl)(phenyl)P—CH$_2$CH$_2$—P(phenyl)$_2$; (phenyl)$_2$PB(phenyl)P(phenyl)$_2$; (phenyl)$_2$PP(phenyl)P(phenyl)$_2$; (phenyl)$_2$PSi(methyl)$_2$P(phenyl)$_2$; (4-chlorophenyl)$_2$PN(isopropyl)P(4-chlorophenyl)$_2$; (4-methoxyphenyl)$_2$PN(methyl)P(4-methoxyphenyl)$_2$; (4-methoxyphenyl)$_2$PN(isopropyl)P(4-methoxyphenyl)$_2$; (3-methoxyphenyl)$_2$PN(methyl)P(3-methoxyphenyl)$_2$; (4-methoxyphenyl)$_2$PN(isopropyl)P(4-methoxyphenyl)(phenyl); (4-methoxyphenyl)(phenyl)PN(isopropyl)P(4-methoxyphenyl)(phenyl); (4-methoxyphenyl)$_2$PN(isopropyl)P(phenyl)$_2$; (4-methoxyphenyl)(phenyl)PN(isopropyl)P(phenyl)$_2$; (4-methoxyphenyl)$_2$P—N(CH$_3$)N(CH$_3$)—P(4-methoxyphenyl)$_2$; (3-methoxyphenyl)$_2$P—N(CH$_3$)N(CH$_3$)—P(3-methoxyphenyl)$_2$; (4-methoxyphenyl)$_2$P—N(CH$_3$)N(CH$_3$)—P(4-methoxyphenyl)(phenyl); (4-methoxyphenyl)(phenyl)P—N(CH$_3$)N(CH$_3$)—P(4-methoxyphenyl)(phenyl); (4-methoxyphenyl)$_2$P—N(CH$_3$)N(CH$_3$)—P(phenyl)$_2$; (4-methoxyphenyl)(phenyl)P—N(CH$_3$)N(CH$_3$)—P(phenyl)$_2$; (4-methoxyphenyl)$_2$P-1,2-benzene-P(4-methoxyphenyl)$_2$; (3-methoxyphenyl)$_2$P-1,2-benzene-P(3-methoxyphenyl)$_2$; (4-methoxyphenyl)$_2$P-1,2-benzene-P(4-methoxyphenyl)(phenyl); (4-methoxyphenyl)(phenyl)P-1,2-benzene-P(4-methoxyphenyl)(phenyl); (4-methoxyphenyl)$_2$P-1,2-benzene-P(phenyl)$_2$; (4-methoxyphenyl)(phenyl)P-1,2-benzene-P(phenyl)$_2$; (3-methoxyphenyl)$_2$P(CH$_2$CH$_2$)P(3-methoxyphenyl)$_2$; (3-methoxyphenyl)$_2$P(CH$_2$CH$_2$)P(3-methoxyphenyl)(phenyl); (3-methoxyphenyl)(phenyl)P(CH$_2$CH$_2$CH$_2$)P(3-methoxyphenyl)(phenyl); (3-methoxyphenyl)(phenyl)P(CH$_2$CH$_2$)P(3-methoxyphenyl)

(phenyl); (3-methoxyphenyl)(phenyl)P(CH$_2$)P(3-methoxyphenyl)(phenyl); (3-methoxyphenyl)$_2$P(CH$_2$CH$_2$)P(phenyl)$_2$; (3-methoxyphenyl)(phenyl)P(CH$_2$CH$_2$)P(phenyl)$_2$; (4-methoxyphenyl)$_2$P(CH$_2$CH$_2$)P(4-methoxyphenyl)$_2$; (4-methoxyphenyl)$_2$P(CH$_2$CH$_2$)P(4-methoxyphenyl)(phenyl); (4-methoxyphenyl)(phenyl)P(CH$_2$CH$_2$CH$_2$)P(4-methoxyphenyl)(phenyl); (4-methoxyphenyl)(phenyl)P(CH$_2$CH$_2$)P(4-methoxyphenyl)(phenyl); (4-methoxyphenyl)(phenyl)P(CH$_2$)P(4-methoxyphenyl)(phenyl); (4-methoxyphenyl)$_2$P(CH$_2$CH$_2$)P(phenyl)$_2$; (4-methoxyphenyl)(phenyl)P(CH$_2$CH$_2$)P(phenyl)$_2$; (2-fluorophenyl)$_2$PN(methyl)P(phenyl)$_2$; (2-fluorophenyl)$_2$PN(n-butyl)P(phenyl)$_2$; (2-fluorophenyl)$_2$PN(n-hexyl)P(phenyl)$_2$; (2-fluorophenyl)$_2$PN(n-decyl)P(phenyl)$_2$; (2-fluorophenyl)$_2$PN(isobutyl)P(phenyl)$_2$; (2-fluorophenyl)$_2$PN(isopropyl)P(phenyl)$_2$; (2-fluorophenyl)$_2$PN(isopentyl)P(phenyl)$_2$; (2-fluorophenyl)$_2$PN(t-butyl)P(phenyl)$_2$; (2-fluorophenyl)$_2$PN(1,2-dimethylpropyl)P(phenyl)$_2$; (2-fluorophenyl)$_2$PN(cyclopropyl)P(phenyl)$_2$; (2-fluorophenyl)$_2$PN(cyclopropylmethyl)P(phenyl)$_2$; (2-fluorophenyl)$_2$PN(allyl)P(phenyl)$_2$; (2-fluorophenyl)$_2$PN(trimethylsityl)P(phenyl)$_2$; (2-fluorophenyl)$_2$PN(pyrollyl)P(phenyl)$_2$; (2-fluorophenyl)$_2$PN(phenyl)P(phenyl)$_2$; (2-fluorophenyl)$_2$PN(naphthyl)P(phenyl)$_2$; (2-fluorophenyl)$_2$PN(methylmorpholine)P(phenyl)$_2$; (2-fluorophenyl)$_2$PN(dimethylamino)P(phenyl)$_2$; (2-fluorophenyl)$_2$PN(benzyl)P(phenyl)$_2$; (2-fluorophenyl)(phenyl)PN(methyl)P(2-fluorophenyl)(phenyl); (2-fluorophenyl)(phenyl)PN(n-hexyl)P(2-fluorophenyl)(phenyl); (2-fluorophenyl)(phenyl)PN(n-decyl)P(2-fluorophenyl)(phenyl); (2-fluorophenyl)(phenyl)PN(isobutyl)P(2-fluorophenyl)(phenyl); (2-fluorophenyl)(phenyl)PN(isopropyl)P(2-fluorophenyl)(phenyl); (2-fluorophenyl)(phenyl)PN(1,2-dimethylpropyl)P(2-fluorophenyl)(phenyl); (2-fluorophenyl)(phenyl)PN(cyclopropyl)P(2-fluorophenyl)(phenyl); (2-fluorophenyl)(phenyl)PN(trimethylsilyl)P(2-fluorophenyl)(phenyl); (2-fluorophenyl)(phenyl)PN(phenyl)P(2-fluorophenyl)(phenyl); (2-fluorophenyl)$_2$PN(methyl)P(2-fluorophenyl)$_2$; (2-fluorophenyl)$_2$PN(n-butyl)P(2-fluorophenyl)$_2$; (2-fluorophenyl)$_2$PN(n-hexyl)P(2-fluorophenyl)$_2$; (2-fluorophenyl)$_2$PN(n-decyl)P(2-fluorophenyl)$_2$; (2-fluorophenyl)$_2$PN(isobutyl)P(2-fluorophenyl)$_2$; (2-fluorophenyl)$_2$PN(isopentyl)P(2-fluorophenyl)$_2$; (2-fluorophenyl)$_2$PN(cyclopropyl)P(phenyl)$_2$; (2-fluorophenyl)$_2$PN(trimethylsilyl)P(2-fluorophenyl)$_2$; (2-fluorophenyl)$_2$PN(phenyl)P(2-fluorophenyl)$_2$; (2-fluorophenyl)$_2$PN(benzyl)P(2-fluorophenyl)$_2$; (2-fluorophenyl)(phenyl)PN(methyl)P(phenyl)$_2$; (2-fluorophenyl)(phenyl)PN(n-decyl)P(phenyl)$_2$; (2-fluorophenyl)(phenyl)PN(isobutyl)P(phenyl)$_2$; (2-fluorophenyl)(phenyl)PN(isopropyl)P(phenyl)$_2$; (2-fluorophenyl)(phenyl)PN(trimethylsilyl)P(phenyl)$_2$; (2-fluorophenyl)(phenyl)PN(benzyl)P(phenyl)$_2$; (2-fluorophenyl)(phenyl)PN(phenyl)P(phenyl)$_2$; (2-fluorophenyl)(phenyl)PN(methylmorpholine)P(phenyl)$_2$; (2-fluoronaphth-1yl)$_2$PN(methyl)P(phenyl)$_2$; (1-fluoronaphth-2-yl)$_2$PN(methyl)P(phenyl)$_2$; (2-fluoronaphth-1-yl)$_2$PN(n-butyl)P(phenyl)$_2$; (1-fluoronaphth-2-yl)$_2$PN(n-hexyl)P(phenyl)$_2$; (2-fluoronaphth-1-yl)$_2$PN(n-decyl)P(phenyl)$_2$; (1-fluoronaphth-2-yl)$_2$PN(isobutyl)P(phenyl)$_2$; (8-fluoronaphth-1-yl)$_2$PN(isopropyl)P(phenyl)$_2$; (8-fluoronaphth-1-yl)$_2$PN(n-hexyl)P(phenyl)$_2$; (8-fluoronaphth-1-yl)$_2$PN(methyl)P(phenyl)$_2$; (2-fluoronaphth-1-yl)$_2$PN(phenyl)P(phenyl)$_2$; (8-fluoronaphth-1-yl)$_2$PN(cyclopropyl)P(phenyl)$_2$; (1-fluoronaphth-2-yl)$_2$PN(benzyl)P(phenyl)$_2$; (8-fluoronaphth-1-yl)$_2$PN(trimethylsilyl)P(phenyl)$_2$; (3-fluoronaphth-2-yl)$_2$PN(hexyl)P(phenyl)$_2$; (3-fluoronaphth-2-yl)$_2$PN(isopropyl)P(phenyl)$_2$; (3-fluoropyrid-4-yl)$_2$PN(methyl)P(phenyl)$_2$; (3-fluoropyrid-4-yl)$_2$PN(n-butyl)P(phenyl)$_2$; (4-fluoropyrid-3-yl)$_2$PN(n-butyl)P(phenyl)$_2$; (3-fluoropyrid-2-yl)$_2$PN(n-butyl)P(phenyl)$_2$; (2-fluoropyrid-3-yl)$_2$PN(n-butyl)P(phenyl)$_2$; (2-fluorophenoxy)$_2$PN(n-butyl)P(phenyl)$_2$; (2-[trifluoromethyl)phenyl)$_2$PN(n-butyl)P(phenyl)$_2$; (2-[trifluoromethyl]phenyl)(phenyl)PN(n-butyl)P(phenyl)$_2$; (2-fluorophenyl)$_2$PN(n-butyl)P(1,2-phenylenedioxy); (2-fluorophenyl)(2-methylphenyl)PN(isopropyl)P(phenyl)$_2$; (2-fluorophenyl)(2-methylphenyl)PN(n-butyl)P(phenyl)$_2$; (2-fluorophenyl)(phenyl) PN(isopropyl)P(phenyl)(2-methylphenyl); (2-fluorophenyl)$_2$PN(n-hexyl)P(ethyl)$_2$; (2-fluorophenyl)$_2$PN(n-hexyl)P(ethyl)(phenyl); (2-fluoroethyl)$_2$PN(n-hexyl)P(phenyl)$_2$; (2,2,2-trifluoroethyl)$_2$PN(n-hexyl)P(phenyl)$_2$; (2-fluorophenyl)$_2$PCH$_2$CH$_2$P(phenyl)$_2$; (2-fluorophenyl)$_2$PN(Me)N(Me)P(phenyl)$_2$; (2-fluorophenyl)(phenyl)PCH$_2$CH$_2$P(phenyl)$_2$; (2-fluorophenyl)(phenyl)PN(Me)N(Me)P(phenyl)$_2$; (2-fluorophenyl)$_2$PCH$_2$N(naphthyl)P(phenyl)$_2$; (2-fluorophenyl)$_2$P(1,2-phenylene)P(phenyl)$_2$; (2-fluorophenyl)$_2$P(1,2-phenylene))P(phenyl)$_2$; (2-methylphenoxy)$_2$PN(n-butyl)P(phenyl)$_2$; 2-methylphenyl)$_2$PN(isopropyl)P(phenyl)$_2$; (2-methylphenyl)$_2$PN(isobutyl)P(phenyl)$_2$; (2-methylphenyl)$_2$PN(n-butyl)P(phenyl)$_2$; (2-methylphenyl)(phenyl)PN(n-hexyl)P(phenyl)$_2$; (2-ethylphenyl)$_2$PN(n-hexyl)P(phenyl)$_2$; (2-ethylphenyl)(phenyl)PN(n-hexyl)P(phenyl)$_2$; (2-methylphenyl)(2-fluorophenyl)PN(isopropyl)P(phenyl)$_2$; (2-methoxyphenyl)$_2$PN(n-butyl)P(phenyl)$_2$; (2-thiomethoxyphenyl)$_2$PN(n-butyl)P(phenyl)$_2$; (2-thiomethoxyphenyl)(phenyl)PN(n-butyl)P(phenyl)$_2$; (2-methylphenyl)$_2$PN(n-hexyl)P(ethyl)$_2$; (2-methylphenyl)$_2$PN(n-hexyl)P(ethyl)(phenyl); (2-methylphenyl)$_2$PN(n-butyl)P(1,2-phenelenedioxy); (2-methylphenyl)$_2$PN(isopropyl)P(1,2-phenelenedioxy); (2-fluorophenyl)$_2$PN(n-butyl)P(1,2-phenelenedioxy); (2-fluorophenyl)$_2$PN(isopropyl)P(1,2-phenelenedioxy); (2-fluorophenyl)$_2$P(1,2-phenylene)P(phenyl)$_2$; (2-methylphenyl)$_2$P(1,2-phenylene)P(phenyl)$_2$; (2-fluorophenyl)$_2$PN(Me)N(Me)P(phenyl)$_2$; (2-methylphenyl)$_2$PN(Me)N(Me)P(phenyl)$_2$; (2-fluorophenyl)$_2$PCH$_2$N(napthyl)P(phenyl)$_2$; (2-methylphenyl)$_2$PCH$_2$N(napthyl)P(phenyl)$_2$.

Activator/Additives (a)(iii):

The above process may include an activator to activate the catalyst. Such an activator is a compound that generates an active catalyst when the activator is combined with the catalyst. These activators may be the same or similar to those found to be useful for activating transition-metal-based olefin polymerisation catalysts, a review of which is provided by Marks [*Chem Rev.* 2000, 100, 1391-1394]. Mixtures of activators may also be used.

Suitable compounds include organoaluminum compounds, organoboron compounds and inorganic acids and salts, such as tetrafluoroboric acid etherate, silver tetrafluoroborate, sodium hexafluoroantimonate and the like. Suitable organoaluminum compounds include compounds of the formula AlR$_3$, where each R is independently C$_1$-C$_{12}$ alkyl, oxygen or halide, and compounds such as LiAlH$_4$ and the like. Examples include trimethylaluminum (TMA), triethylaluminum (TEA), tri-isobutylaluminium (TIBA), tri-n-octylaluminium, methylaluminium dichloride, ethylaluminium dichloride, dimethylaluminium chloride, diethylaluminium chloride, ethylaluminiumsesquichloride, methylaluminiumsesquichloride, and aluminoxanes. Aluminoxanes are well known in the art as typically oligomeric compounds which can be prepared by the controlled addition of water to an alkylaluminium compound, for example trimethylaluminium. Such compounds can be linear, cyclic, cages or mixtures thereof. Commercially available aluminoxanes are generally believed to be mixtures of linear and cyclic compounds. The cyclic aluminoxanes can be represented by the formula $[R^{11}AlO]_s$ and the linear aluminoxanes by the formula $R^{12}(R^{13}AlO)_s$ wherein s is a number from about 2 to 50, and wherein $R^{11}$, $R^{12}$, and $R^{13}$ represent hydrocarbyl groups, typically $C_1$ to $C_8$ alkyl groups, for example methyl, ethyl or butyl groups. Alkylaluminoxanes especially methylaluminoxane (MAO) are particularly suitable. (MAO is also referred to as methalumoxane and methylalumoxane in the literature).

It will be recognized by those skilled in the art that commercially available alkylaluminoxanes may contain a proportion of trialkylaluminium. For instance, commercial MAO usually contains approximately 10 wt % trimethylaluminium (TMA), and commercial "modified MAO" (or "MMAO") contains both TMA and TIBA. Quantities of alkylaluminoxane are generally quoted herein on a molar basis of aluminum (and include such "free" trialkylaluminium). The alkylaluminoxane and/or alkylaluminium may be added to the reaction media (i.e. ethylene and/or diluent and/or solvent) prior to the addition of the catalyst or at the same time as the catalyst is added. Such techniques are known in the art of oligomerization and are disclosed in more detail in for example, U.S. Pat. Nos. 5,491,272; 5,750,817; 5,856,257; 5,910,619; and 5,919,996 as well as WO 2008/146215 and WO 2007/007272.

In the preparation of the catalyst systems used in the present invention, the optimal quantity of activating compound to be employed is easily determined by simple testing, for example, by the preparation of small test samples which can be used to oligomerize small quantities of ethylene and thus to determine the activity of the produced catalyst. It is generally found for alkylaluminium and aluminoxane based activators or co-activators that a suitable quantity employed is 0.5 to 2000 moles of aluminum per mole of chromium.

Examples of suitable organoboron activator compounds are boroxines, $NaBH_4$, trimethylboron, triethylboron, triphenylboron, dimethylphenylammoniumtetra(phenyl)borate, tritytetra(phenyl)borate, dimethylphenylammonium tetrakis(pentafluorophenyl)borate, trityl tetrakis(pentafluorophenyl)borate, tris(pentafluorophenyl)boron, sodium tetrakis[(bis-3,5-trifluoromethyl)phenyl]borate, dimethyiphenylammonium tetrakis[(bis-3,5-trifluoromethyl)phenyl]borate, and trityl tetrakis[(bis-3,5-trifluoromethyl)phenyl]borate.

Those skilled in the art will recognise that boron-containing activators are commonly used in combination with aluminum alkyl activators.

In some embodiments organoboron activators, as described in WO 2010/092554, include a cation and a non-coordinating anion of the general formula

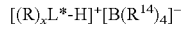

wherein:
L* is an atom selected from the group consisting of N, S and P;
the cation $[(R)_xL^*-H]^+$ is a Bronsted acid;
x is an integer 1, 2 or 3;
each R is the same or different and each is a —H, hydrocarbyl group or a heterohydrocarbyl group;
provided that at least one of R comprises at least 6 carbon atoms and provided further that the total number of carbon atoms in $(R)_x$ collectively is greater than 12;
$R^{14}$ independently at each occurrence is selected from the group consisting of hydride, dialkylamido, halide, alkoxide, aryloxide, hydrocarbyl, halosubstituted-hydrocarbyl radicals, halosubstituted-alkoxide, halosubstituted-aryloxide and a halosubstituted aromatic moiety with at least one halide substituent on the aromatic moiety.

Illustrative, but non-limiting examples of these organoboron activators include methyldi(octadecyl)ammonium tetrakis(pentafluorophenyl)borate and trioctylammonium tetrakis(pentafluorophenyl)borate.

The source of chromium and the organoboron activator may be combined in proportions to provide organoboron compound/chromium molar ratios from about 0.1 to 50 organoboron to 1 chromium, or from about 0.8 to 20 organoboron to 1 chromium, or from 1 to 10 organoboron to 1 chromium.

In some embodiments activators, as described in WO 2007/039851, include a cation and an anion component, and may be represented by the following formula:

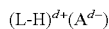

where L is a neutral Lewis base; H is hydrogen; $(L-H)^{d+}$ is a Bronsted acid; $A^{d-}$ is a non-coordinating anion having the charge d−; and d is an integer from 1 to 3.

In these activator compounds, $A^{d-}$ can be a fluorinated aluminate group. Illustrative but non-limiting examples of the anion component $A^{d-}$ are $[Al\{OC(CF_3)_3\}_4]^-$; $[Al(OC_6F_5)_4]^-$; $[Al(C_6F_4O_2)_2]^-$; $[AlF\{OC(CF_3)_3\}_3]^-$; $[Al_2F\{OC(CF_3)_3\}_6]^-$; and $[Ta(OC_6F_5)_6]^-$.

The activator compound may optionally be a solid material, or be supported on an insoluble solid material. For example, aluminoxanes such as MAO and borate activators may be supported on inorganic oxides such as alumina, silica, $MgCl_2$ or the like.

The process may further include the use of compounds that may act as a reducing or oxidising agent, such as sodium or zinc metal and the like, or an oxygen-containing compound, for example oxygen and the like. Additionally, hydrogen ($H_2$) and/or silanes and the like may be used in the catalytic composition or otherwise added to the process. The process may also include the use of a zinc species as an additive, as described in WO 2011/048527, which is herein incorporated by reference. Preferred zinc species would be dialkyl zinc reagents such as dimethylzinc or diethylzinc.

Catalyst Preparation:

The chromium (i) and ligand (ii) may be present in any molar ratio which produces oligomer, and in some embodiments is between 100:1 and 1:100, or from 10:1 to 1:10, or from 3:1 to 1:3. Generally the amounts of (i) and (ii) are approximately equal, i.e. a ratio of between 1.5:1 and 1:1.5.

The ligand, chromium and activators of the catalyst system utilized in the present invention may be added together simultaneously or sequentially, in any order, and in the presence or absence of ethylene or other unsaturated hydrocarbon in any suitable solvent at any suitable concentration, so as to give an active catalyst. For example, the ligand, chromium, activators and ethylene may be contacted together simultaneously; or the ligand, chromium and activators may be added together simultaneously or sequentially in any order and then contacted with ethylene; or chromium and the ligand may be added together to form an isolable metal-ligand complex and then added to the activator and contacted with ethylene; or the ligand, chromium and activators/co-activators may be added together to form an isolable metal-ligand complex and then contacted with ethylene.

Any or all of the chromium source, ligating compound and activator components utilized in the present invention can be unsupported or supported on a support material, for example silica, alumina, MgCl$_2$ or zirconia, or on a polymer, for example polyethylene, polypropylene, polystyrene or poly(aminostyrene).

Diluent:

The process of the present invention may be carried out in the presence or absence of an added diluent. In some embodiments of the invention the diluents include oligomerisation products e.g. 1-octene and/or 1-hexene, aliphatic and aromatic hydrocarbon solvents and halogenated-aromatic solvents such as chlorobenzene, dichlorobenzene, fluorobenzene and the like. In some embodiments the diluents are aliphatic hydrocarbon solvents including but not limited to Isopar™, iso-octane, cyclohexane, cyclopentane, methylcyclohexane, propane, isobutane, isopentane, neopentane, 2-methylpentane, or 3-methylpentane.

Alternatively the process can be conducted as a bulk process in which essentially neat reactant and/or product olefins serve as the dominant medium.

Process Conditions:

The tetramerization is conducted under solution phase conditions, which is herein taken to mean that any polymer co-product remains substantially dissolved in the liquid reaction medium under the chosen reaction conditions.

The formation of a high molecular weight polymer co-product by the Cr-based ethylene tetramerisation catalyst may present a major technical challenge when commercialising an ethylene tetramerisation process. Polymer fouling of the reactor or downstream sections may reduce plant run time and necessitate shut-downs due to blockages and loss of reaction cooling due to coating of heat exchange surfaces. When running tetramerisation processes at reaction temperatures in the range of 40 to 80° C., as is taught in the art, most of the polymer co-product precipitates in the reactor, which can result in fouling of process equipment. To ensure process reliability and adequate run-times under such reaction conditions, it may be necessary to utilise expensive or energy-intensive process design features.

Running a tetramerisation process at process conditions whereby the polymer co-product remains predominantly dissolved in the liquid reaction medium in the reactor (i.e. a solution phase process) would substantially reduce the possibility of reactor or downstream fouling. In addition, a further benefit of such a process might be that a cheaper or more energy-efficient process design could be used, due to the reduced likelihood of fouling process equipment. A solution phase process could be achieved by using higher reaction temperatures than typically taught in the art. However, the art teaches away from running at higher temperatures due to undesirable effects including poor catalyst activity, increased polymer formation and increased selectivity towards 1-hexene.

Given the high molecular weight nature of the polymer co-product produced in a tetramerisation process under the preferred process conditions taught in the art, a person skilled in the field of polymerisation processes would conclude that reaction temperatures of greater than 150° C. would be required to achieve a solution phase tetramerisation process. At such temperatures, the problems of catalyst deactivation and octene selectivity loss would render the process unfeasible. Surprisingly, it has now been found that a solution phase tetramerisation process can be achieved at temperatures from above 80° C. to 115° C., while maintaining acceptable catalyst activities and 1-octene selectivities. In some embodiments the temperature range is between 85° C. and 110° C., preferably 85° C. to 100° C. whilst in other embodiments the temperature range is between 90° C. and 105° C. In some embodiments the temperature range is from above 80° C. or above 85° C. or above 90° C. to about 115° C. or about 110° C. or about 105° C. or about 100° C.

Suitable reaction pressures are from atmospheric to 800 atmospheres, or from 5 atmospheres to 100 atmospheres, or from 40 to 100 atmospheres, or from 60 to 100 atmospheres. The negative effect of higher reaction temperatures on selectivity towards 1-octene can partially be reversed through the use of higher reaction pressures, together with the catalysts and reaction temperature ranges of the present invention.

In one embodiment, the continuous process for the tetramerisation of ethylene is a process where the reactors are run continuously. By this it is meant herein that the reactors, when operating, are run in continuous mode, that is at least one feed stream is predominantly fed continuously to the reactor, while at least one stream is predominantly withdrawn continuously. Reactors utilizing both CSTR and plug flow behavior may be considered. There are different potential configurations as a subset of these two types of reactors. For example, CSTR type reactors include bubble columns, stirred tanks, loop reactors with single or two phases while plug flow reactors include fixed bed and homogeneous tubular types of varying residence times. Any of the aforementioned reactor types may be operated with liquid or vapour and liquid-continuous phase flow. As a further subset, reactors can be configured with different cooling options such as internal or external heat exchangers, interstage coolers, and cold feed heat removal amongst others. There is opportunity to configure the same reactor several times in series or use combinations of different reactor types and cooling techniques together to achieve the desired result.

For systems where tetramerisation takes place in the liquid phase, different mass transfer opportunities exist including jet loop mixing, bubble column sparging, tubular reactor multiple injections and pre-saturation of the feed material amongst others.

The reactor type selected may depend on factors such as heat removal, mechanical robustness with regard to fouling, residence time distributions, product composition effects as a result of secondary reactions and mechanical equipment cost implications. In a process where polymer precipitates out of the reaction medium, the selection criteria of heat removal and mechanical robustness with regard to fouling may be expected to dominate and many reactor configurations may therefore be excluded. In a solution phase process, a wider range of reactor configurations may be considered and implemented to optimize factors such as residence time distributions, product composition effects as a result of secondary reactions and mechanical equipment cost implications. In particular, the use of reactors wherein reaction cooling is effected by means of heat exchangers in contact with the reaction medium may be practical in a solution phase process, whereas the susceptibility of such heat exchangers to fouling may rule out such options for a slurry-phase process.

Composition and Properties of the Tetramerisation Process Products:

It has now surprisingly been found that a particularly favourable and novel product composition is achieved when running a tetramerisation process at temperatures from above 80° C. to 115° C. This composition includes both a valuable product for sale, i.e. 1-octene, as well as a polymer co-product having properties which reduce the tetramerisation process complexity, cost and risk relative to a tetramerisation process performed at the preferred, lower reaction temperatures as taught in the prior art.

The polyethylene co-product is characterised by having a comparatively low molecular weight as measured by gel permeation chromatography and low melt viscosity as measured by a high melt flow index measurement. As such, it differs substantially from the polyethylene produced in tetramerisation processes conducted at or below 80° C., and also from polyethylene produced in commercial solution phase polyethylene processes at much higher temperatures.

The polyethylene co-product has a weight average molecular weight (Mw), as determined by gel permeation chromatography, of less than 200 000 g/mol. In some embodiments of the invention the weight average molecular weight (Mw), as determined by gel permeation chromatography, is less than 150 000 g/mol. In some embodiments of the invention the weight average molecular weight (Mw), as determined by gel permeation chromatography, is less than 100 000 g/mol. In some embodiments of the invention the weight average molecular weight (Mw), as determined by gel permeation chromatography, is less than 50 000 g/mol.

The polyethylene co-product has a number average molecular weight (Mn), as determined by gel permeation chromatography, of less than 3 000 g/mol. In some embodiments of the invention the number average molecular weight (Mn), as determined by gel permeation chromatography, is less than 2 500 g/mol. In some embodiments of the invention the number average molecular weight (Mn), as determined by gel permeation chromatography, is less than 2 000 g/mol. In some embodiments of the invention the number average molecular weight (Mn), as determined by gel permeation chromatography, is less than 1 900 g/mol.

The polyethylene co-product has a melt flow index, as determined by ASTM method D1238 at 190° C. and 21.6 kg weight, of more than 20 g/10 minutes. In some embodiments of the invention, the polyethylene co-product has a melt flow index, as determined by ASTM method D1238 at 190° C. and 21.6 kg weight, of more than 35 g/10 minutes. In some embodiments of the invention, the polyethylene co-product has a melt flow index, as determined by ASTM method D1238 at 190° C. and 21.6 kg weight, of more than 50 g/10 minutes. In some embodiments of the invention, the polyethylene co-product has a melt flow index, as determined by ASTM method D1238 at 190° C. and 21.6 kg weight, of more than 60 g/10 minutes.

The novel resulting tetramerisation process product composition, comprising at least 30% 1-octene together with a polyethylene co-product having improved properties, allows a commercially viable solution phase tetramerisation process to be realised, in which good catalyst activities and reasonable 1-octene selectivities may be achieved while simultaneously keeping all the products substantially dissolved in the liquid reaction medium. Such a process, when operated continuously, will be substantially less prone to reactor and downstream fouling than a tetramerisation process conducted at reaction temperatures of at or below 80° C., as taught in the art. The lower molecular weight of the polymer co-product will also improve the processability of this material downstream of the reactor, for example in flash vessels as described in WO 2011/045701. In addition, any fouling of process equipment by a lower molecular weight polymer co-product may be easier, cheaper and less time-consuming to clean, for example by hot-washing.

The reduced risk of fouling, the potentially simpler and lower cost process design and the improved polymer processability would make a high temperature, solution phase tetramerisation process highly advantageous.

Catalyst Performance

The catalysts of the present invention can operate at higher temperatures with good catalyst activity, while maintaining acceptable selectivities towards 1-octene and low levels of polymer formation. In some embodiments of the invention the average activity of these catalysts is greater than 700 000 g/gCr/h at 100° C., 45 bar, or greater than 1 000 000 g/gCr/h at 100° C., 45 bar, or greater than 2 000 000 g/gCr/h at 100° C., 45 bar, or greater than 3 000 000 g/gCr/h at 100° C., 45 bar.

In some embodiments the catalyst produces at least 35 mass % 1-octene at 100° C., 45 bar ethylene, or at least 45 mass % 1-octene at 100° C., 45 bar ethylene. In some embodiments the catalyst produces less than 4 mass % polymer co-product, or less than 3 mass % polymer co-product, or less than 2 mass % polymer co-product.

The invention will now be described in more detail, by way of example only, with reference to the following non-limiting examples.

EXAMPLES

The following abbreviations are used in the examples:
PCl chlorophosphine
Et ethyl
iPr isopropyl
nBu normal-butyl
1,2-DMP 1,2-dimethylpropyl
MCPE 1-(1-methylcyclopropyl)ethyl
Ph phenyl
PNH phosphinoamine, e.g. $Ar_2PN(R)H$, where Ar is an aryl, and R is an organyl group
PNP bis phosphinoamine, e.g. $Ar_2PN(R)PAr_2$, where Ar is an aryl, and R is an organyl group
oFPh ortho-fluorophenyl
DCM dichloromethane
THF tetrahydrofuran
MMAO-3A An aluminoxane product General Experimental Conditions for Ligand Synthesis All reactions were carried out under an argon atmosphere using a dual vacuum/nitrogen line and standard Schlenk techniques. Solvents were purified via a Braun solvent purification system. All reagents purchased from commercial suppliers were used without further purification. NMR spectra were recorded on a Varian 400 MHz spectrometer using $CDCl_3$. PNP compounds below were prepared by modification of the procedure described in *Synthesis*, 2007, 24, 3863.

Preparation of ortho-fluorophenylmagnesium bromide: (o-FPh)MgBr

A dry and argon flushed Schlenk was charged with iPrMgCl.LiCl (1.42 g, 7.5 mmol, 1.3 M solution in THF). The solution was cooled in an ice bath and 1-bromo-2-fluorobenzene (1.31 g, 7.5 mmol) was added dropwise. The reaction mixture was stirred for 1 hr and the resulting Grignard product was used in the next step as described below.

Preparation of the di(o-fluorophenyl)phosphinechloride: $(o-FPh)_2PCl$

The Grignard reagent o-FPhMgBr (from above) was slowly added to a pre-cooled solution of $PCl_3$ (0.52 g, 3.8 mmol) in anhydrous THF (10 ml) at room temperature. After addition was complete, the suspension was stirred at room temperature for a further 1 h after which the reaction was complete as judged by $^{31}$P NMR ($\delta$ 61.1 (t, J=64.5 Hz)). The product was used in the next step without isolation.

Ligand Preparation Example 1

Preparation of (2-fluorophenyl)$_2$PN(iPr)PPh$_2$ iPrNH$_2$ (0.5 g, 8.46 mmol) and Et$_3$N (1.71, 16.9 mmol) were added to the crude (o-FPh)$_2$PCl compound (1.81g, 7.1 mmol) [prepared as described above] in diethyl ether (10 ml). The reaction mixture was stirred at room temperature until complete formation of the PNH intermediate. The volatiles were removed in vacuo. Ether (50 ml) was added and the resultant mixture filtered to give the ether solution of the desired PNH product in reasonable purity [by $^{31}$P NMR analysis: $\delta$ 15.7 (t, J=33.4 Hz)]. The solvent was evaporated off to give the PNH molecule (0.8 g, 2.9 mmol) which was re-dissolved in DCM (10 ml). Et$_3$N (0.56 g, 5.9 mmol) was added followed by incremental addition of Ph$_2$PCl (1.3 g, 5.9 mmol) at room temperature. After complete conversion of the PNH (judged by $^{31}$P NMR analysis) to the PNP, the post reaction mixture was concentrated. Ether (100 ml) was added and the resultant mixture was filtered through a short activated alumina column. Filtration was repeated until a pure compound was obtained. The solvent was evaporated to give the desired PNP product. $^1$H NMR (CDCl$_3$): $\delta$ 7.49-6.82 (m, 18H, Ar), 3.79 (m, 1H, CH), 1.10 (d, 6H, J=6.8 Hz, CH$_3$). $^{19}$F NMR (CDCl$_3$): $\delta$ 103.2 (d, J=49.0 Hz). $^{31}$P NMR (CDCl$_3$): $\delta$ 52.5 (br s), 22.6 (br s).

Ligand Preparation Example 2

Preparation of (2-fluorophenyl)$_2$PN(nBu)PPh$_2$

This compound was prepared following the procedure described in ligand example 1 above, except that nBuNH$_2$ instead of iPrNH$_2$ was used. $^1$H NMR (CDCl$_3$): $\delta$ 7.45-6.93 (m, 18H, Ar), 3.31 (m, 2H, CH$_2$), 1.21 (m, 1H, CH), 0.58 (d, 6H, J=6.8 Hz, CH$_3$). $^{31}$P NMR (CDCl$_3$): $\delta$ 63.2 (d, J=41.6 Hz), 39.0 (m).

Catalyst Preparation Example 3

Preparation of [(dppb)CrCl$_2$]$_2$($\mu$-Cl)$_2$ (dppb=Ph$_2$P(1,2-phenylene)PPh$_2$)

This complex was prepared by reaction of Ph$_2$P(1,2-phenylene)PPh$_2$ (purchased from Sigma Aldrich) and Cr(THF)$_3$Cl$_3$ (purchased from Sigma Aldrich) as described in Journal of Molecular Catalysis A: Chemical 283 (2008) 114-119.

Ligand Preparation Comparative Example 1

Preparation of (phenyl)$_2$PN(1,2-DMP)P(phenyl)$_2$

This compound was prepared from the reaction of (1,2-DMP)NH$_2$ (1.0 g, 13.7 mmol), Et$_3$N (5.54 g, 54.7 mmol), Ph$_2$PCl (7.59 g, 41.0 mmol), following a procedure described in *Synthesis*, 2007, 24, 3863. $^{31}$P NMR (CDCl$_3$): $\delta$ 54 (br s).

Ligand Preparation Comparative Example 2

Preparation of (phenyl)$_2$PN(MCPE)P(phenyl)$_2$

This compound was prepared from the reaction of (MCPE)NH$_2$ (1.0 g, 13.7 mmol), Et$_3$N (5.54 g, 54.7 mmol), Ph$_2$PCl (7.59 g, 41.0 mmol), following a procedure described in *Synthesis*, 2007, 24, 3863. $^{31}$P NMR (CDCl$_3$): $\delta$ 49-58 (br s).

Example 1

Continuous ethylene tetramerisation with (2-fluorophenyl)$_2$PN(iPr)PPh$_2$ at 100° C. and 40 bar A 5000 ml stainless steel continuous reactor system, equipped with a sight-glass, was inertised by heating under vacuum, and refilling with N$_2$. The reactor was charged with methylcyclohexane (2000 ml) and MMAO-3A, and pressurised to 40 bar with ethylene. A solution of Cr(acac)$_3$ (83 µmol/litre) and (2-fluorophenyl)$_2$PN(iPr)PPh$_2$ (83 µmol/litre) in methylcyclohexane, and a solution of MMAO-3A (27 mmol Al/litre) in methylcyclohexane were then both fed continuously to the reactor, so as to maintain an Al:Cr ratio of approximately 1000:1 in the reactor. The reactor was cooled by means of a water-cooled jacket to maintain a constant temperature of 100° C. throughout the run. The reaction pressure was kept constant at 40 bar throughout the run by feeding ethylene on demand, and the consumption of ethylene was monitored via a flow meter. H$_2$ and ZnEt$_2$ additives were added to the reactor as well. A continuous drain of the reactor was employed to ensure a stable liquid level within (liquid volume of 2500 ml), and methylcyclohexane was added continuously to maintain the targeted residence time and product:diluent ratio. The reactor drainings were cooled and depressurised in a vent pot, and then drained into a drum and weighed. A small sample was taken for GC-FID analysis. The polymer by-product, which precipitated out of the cooled reaction mixture, was collected by filtration, dried overnight and weighed. The reaction selectivity and activity were then calculated from the catalyst flow rates, the ethylene consumption, the GC data, the recovered mass of product and the recovered polymer mass. It was observed through the sight-glass that the reaction mixture was homogeneous—the polyethylene co-product was substantially dissolved in the liquid medium. After 5.5 hours of operation, the reaction was terminated, and the reactor was drained. Only 1.7 g of polymer remained on the reactor walls after the run (2.4% of the polymer formed in the run). The activity and selectivity results are shown in Table 1.

Example 2

Continuous ethylene tetramerisation with (2-fluorophenyl)$_2$PN(iPr)PPh$_2$, (2-fluorophenyl)$_2$PN(nBu)PPh$_2$ and Ph$_2$P(1,2-phenylene)PPh$_2$ at 100° C. and 40 bar The procedure of example 1 was followed, except that after 5.7 hours of continuous reaction, the ligand being fed to the reactor was switched from (2-fluorophenyl)$_2$PN(iPr)PPh$_2$ to (2-fluorophenyl)$_2$PN(nBu)PPh$_2$ and the reaction temperature was reduced to 95° C., and after 8.0 hours of continuous operation, the catalyst was switched from Cr(acac)$_3$/(2-fluorophenyl)$_2$PN(nBu)PPh$_2$ to [(dppb)CrCl$_2$]$_2$ ($\mu$-Cl)$_2$ (dppb=Ph$_2$P(1,2-phenylene)PPh$_2$). It was observed through the sight-glass that the reaction mixture was homogeneous—the polyethylene co-product was substantially dissolved in the liquid medium throughout the run. After 10 hours of operation, the reaction was terminated, and the reactor was drained. Only 0.7 g of polymer remained on the reactor walls after the run (1.0% of the polymer formed in the run). The activity and selectivity results are shown in Table 1.

Example 3

Continuous ethylene tetramerisation with (2-fluorophenyl)$_2$PN(nBu)PPh$_2$ at 95° C. to 90° C. and 40 bar The procedure of example 1 was followed, except that the ligand (2-fluorophenyl)$_2$PN(nBu)PPh$_2$ was used, and the reaction temperature was maintained at 95° C. and then lowered to 90° C. after 9.5 hours. It was observed through the sight-glass that the reaction mixture remained homogeneous throughout—the polyethylene co-product was substantially dissolved in the liquid medium throughout the run. After 12 hours of operation, the reaction was terminated, and the reactor was drained. Only 2.4 g of polymer remained on the reactor walls after the run (0.8% of the polymer formed in the run). The activity and selectivity results are shown in Table 1.

Comparative Example 2

Continuous ethylene tetramerisation with Ph$_2$PN(MCPE)PPh$_2$ at 70° C. and 40 bar The procedure of example 1 was followed, except that the ligand Ph$_2$PN(MCPE)PPh$_2$ was used, the reaction diluent was 2,2,4-trimethylpentane, ZnEt$_2$ was not added, and a reactor temperature of 70° C. was used. It was observed through the sight-glass that the reaction mixture was a heterogeneous slurry—the polyethylene co-product was substantially present as a precipitate in the liquid medium. After 18 hours of operation, the reaction was terminated, and the reactor was drained. 72 g of polymer remained on the reactor walls after the run (59% of the polymer formed in the run). The activity and selectivity results are shown in Table 1.

TABLE 1

Catalytic results to demonstrate the present invention

| Example | Time on stream (min) | Catalyst | Temp (° C.), Press. (bar) | Average Activity (×10$^6$ g/gCr/h) | 1-Hexene selectivity (mass %) | 1-Octene selectivity (mass %) | Polymer selectivity (mass %) | 1-Octene:1-Hexene ratio (g/g) |
|---|---|---|---|---|---|---|---|---|
| 1 | 80-200 | Cr(acac)$_3$/(2-FPh)$_2$PN(iPr)PPh$_2$/MMAO-3A | 100, 40 | 1.2 | 47.3 | 36.1 | 1.1 | 0.76 |
|   | 200-320 | Cr(acac)$_3$/(2-FPh)$_2$PN(iPr)PPh$_2$/MMAO-3A | 100, 40 | 3.0 | 43.6 | 36.4 | 1.5 | 0.83 |
| 2 | 120-340 | Cr(acac)$_3$/(2-FPh)$_2$PN(iPr)PPh$_2$/MMAO-3A | 100, 40 | 2.0 | 45.1 | 38.9 | 1.9 | 0.86 |
|   | 340-480 | Cr(acac)$_3$/(2-FPh)$_2$PN(nBu)PPh$_2$/MMAO-3A | 95, 40 | 1.5 | 36.9 | 45.6 | 3.1 | 1.23 |
|   | 520-600 | [(dppb)CrCl$_2$]$_2$(µ-Cl)$_2$/MMAO-3A | 95, 40 | 0.9 | 49.6 | 36.6 | 1.2 | 0.74 |
| 3 | 240-720 | Cr(acac)$_3$/(2-FPh)$_2$PN(nBu)PPh$_2$/MMAO-3A | 95-90, 40 | 2.3 | 35.4 | 45.5 | 7.0 | 1.30 |
| Comp 1 | 180-300 | Cr(acac)$_3$/Ph$_2$PN(1,2-DMP)PPh$_2$/MMAO-3A | 60, 40 | 4.0 | 25.9 | 58.9 | 1.0 | 2.27 |
| Comp 2 | 480-1060 | Cr(acac)$_3$/Ph$_2$PN(MCPE)PPh$_2$/MMAO-3A | 70, 40 | 4.1 | 33.7 | 50.4 | 1.5 | 1.50 |

Comparative Example 1

Continuous ethylene tetramerisation with Ph$_2$PN(1,2-DMP)PPh$_2$ at 60° C. and 40 bar The procedure of example 1 was followed, except that the ligand Ph$_2$PN(1,2-DMP)PPh$_2$ and a reactor temperature of 60° C. was used. It was observed through the sight-glass that the reaction mixture was a heterogeneous slurry—the polyethylene co-product was substantially present as a precipitate in the liquid medium. After 6 hours of operation, the reaction was terminated, and the reactor was drained. 13 g of polymer remained on the reactor walls after the run (44% of the polymer formed in the run). The activity and selectivity results are shown in Table 1.

Polymer Characterisation

The polymer that was present as a suspension/precipitate in the cooled and depressurised reaction product was isolated by vacuum filtration, and dried in air. Before the submission of polymer for analysis, the samples were ground to a homogeneous powder to ensure consistency and representativity of the entire bulk sample obtained.

High Temperature Gel Permeation Chromatography (GPC) analyses were performed on a Polymer Laboratories GPC220 instrument. Single solutions of each sample were prepared by adding 15 mL of 1,2,4-trichlorobenzene solvent to 3.75, 7.5 or 15 mg of sample. The samples were heated at 190° C. for 20 minutes whilst shaking, then cooled to 160° C. The solutions were filtered through a 1 µm glass fiber mesh at 160° C. The filtered solutions were analysed in duplicate enabling a measure of quality of measurement and inherent instrumentation error (quantified previously). The GPC system is calibrated for linear polystyrene, with absolute Mw quantification of polymer samples expressed as for linear polyethylene (by adjustment with literature viscosity constants).

Melt Flow Index (MFI) measurements are conducted according to a standard ASTM D-1238 method [A. Furumiya, Y. Akana, Y. Ushida, T. Masuda and A. Nakajima, *Relationship between molecular characteristics and physical properties of linear low density polyethylene.* Pure & Applied Chemistry 6, vol 57, 823-832 (1985)] using a Ceast DAS 4000 WIN instrument. The MFI instrument consists of a small 2 mm diameter die inserted into the extruder. The samples were loaded into the instrument and preheated for 5 min at 190° C., after which a weight of 21.6 kg was introduced. This weight exerts a shear force on the molten polymer and it immediately starts flowing through the die. The flow rate of the molten polymer is then measured. The MFI measurement is expressed as grams of polymer/10 minutes of flow time, for the given weight applied.

The polymer characterisation data are shown in Table 2.

TABLE 2

Characterisation data for polyethylene co-product produced in the continuous tetramerisation examples.

| Example | Polymer from time on stream (min) | Catalyst | Temp (° C.), Press. (bar) | Mw (g/mol) | Mn (g/mol) | MFI - 21.6 kg (g/10 min) |
|---|---|---|---|---|---|---|
| 1 | 80-320 | Cr(acac)$_3$/(2-FPh)$_2$PN(iPr)PPh$_2$/MMAO-3A | 100, 40 | 14 500 | 1 270 | 81.3 |
| 2 | 280-460 | i) Cr(acac)$_3$/(2-FPh)$_2$PN(iPr)PPh$_2$, MMAO-3A ii) Cr(acac)$_3$/(2-FPh)$_2$PN(nBu)PPh$_2$, MMAO-3A | 95, 40 | 29 000 | 1 860 | 73.1 |
| 2 cont. | 460-600 | [(dppb)CrCl$_2$]$_2$(μ-Cl)$_2$/MMAO-3A | 95, 40 | 10 400 | 1 230 | 70.3 |
| 3 | 240-620 | Cr(acac)$_3$/(2-FPh)$_2$PN(nBu)PPh$_2$/MMAO-3A | 95-90, 40 | 16 800 | 1 770 | 75.3 |
| Comp1 | 60-360 | Cr(acac)$_3$/Ph$_2$PN(1,2-DMP)PPh$_2$/MMAO-3A | 60, 40 | 325 000 | 4 700 | 5.33 |
| Comp 2 | 80-1060 | Cr(acac)$_3$/Ph$_2$PN(MCPE)PPh$_2$/MMAO-3A | 70, 40 | 516 000 | 5 640 | 0.56 |

What is claimed is:

1. A continuous process for the tetramerisation of ethylene, the process including:
   providing an activated catalyst comprising:
   i) a source of chromium;
   ii) a ligating compound of the formula $R^1R^2P^1XP^2R^3R^4$ wherein $P^1$ and $P^2$ are phosphorus atoms;
   X is a linking group between $P^1$ and $P^2$, such that any heteroatom on the shortest connecting path between $P^1$ and $P^2$ is either bound to $P^1$ or $P^2$ or adjacent to an atom bound to $P^1$ or $P^2$; and
   $R^1$ to $R^4$ are independently a hydrocarbyl group, an organoheteryl group or a heterohydrocarbyl group; and iii) optionally a catalyst activator or combination of catalyst activators; and
   b) contacting ethylene to be tetramerised with the activated catalyst at a reaction temperature of from above 80° C. to about 115° C., thereby to form at least 30% 1-octene and a polyethylene co-product that, together with any other reaction products, remain substantially dissolved in the liquid phase, the polyethylene co-product being characterised as having:
   i) a weight average molecular weight (Mw), as determined by gel permeation chromatography, of less than 200 000 g/mol;
   ii) a number average molecular weight (Mn), as determined by gel permeation chromatography, of less than 3 000 g/mol; and
   iii) a melt flow index, as determined by ASTM method D1238 at 190° C. and 21.6 kg, of more than 20 g/10 minutes.

2. A continuous process according to claim 1, wherein the ethylene is contacted with the activated catalyst at a reaction temperature of from above 85° C. to about 110° C.

3. A continuous process according to claim 1, wherein the ethylene is contacted with the activated catalyst at a reaction temperature of from above 90° C. to about 105° C.

4. A continuous process according to claim 1, wherein the polyethylene has:
   i) a weight average molecular weight (Mw), as determined by gel permeation chromatography, of less than 150 000 g/mol;
   ii) a number average molecular weight (Mn), as determined by gel permeation chromatography, of less than 2 500 g/mol; and
   iii) a melt flow index, as determined by ASTM method D1238 at 190° C. and 21.6 kg, of more than 35 g/10 minutes.

5. A continuous process according to claim 1, wherein the polyethylene has:
   i) a weight average molecular weight (Mw), as determined by gel permeation chromatography, of less than 100 000 g/mol;

ii) a number average molecular weight (Mn), as determined by gel permeation chromatography, of less than 2 000 g/mol; and iii) a melt flow index, as determined by ASTM method D1238 at 190° C. and 21.6 kg, of more than 50 g/10 minutes.

6. A continuous process according to claim 1, wherein the polyethylene has:
i) a weight average molecular weight (Mw), as determined by gel permeation chromatography, of less than 50 000 g/mol;
ii) a number average molecular weight (Mn), as determined by gel permeation chromatography, of less than 1 900 g/mol; and
iii) a melt flow index, as determined by ASTM method D1238 at 190° C. and 21.6 kg, of more than 60 g/10 minutes.

7. A continuous process according to claim 1, wherein at least one of $R^1$ to $R^4$ is an aromatic moiety or a heteroaromatic moiety.

8. A continuous process according to claim 1, wherein $R^1$ to $R^4$ are all aromatic or heteroaromatic moieties.

9. A continuous process according to claim 1, wherein $R^1$ to $R^4$ are all optionally substituted phenyl groups.

10. A continuous process according to claim 1, wherein at least one of $R^1$ to $R^4$ is an aromatic moiety of which a ring atom of the aromatic ring structure is bound to either $P^1$ or $P^2$ and which has a polarising substituent bound to a ring atom of the aromatic ring structure adjacent to the ring atom bound to $P^1$ or $P^2$.

11. A continuous process according to claim 10, wherein the polarising substituent bound to a ring atom of the aromatic ring structure adjacent to the ring atom bound to $P^1$ or $P^2$ includes methoxy, ethoxy, isopropoxy, $C_3$-$C_{20}$ alkoxy, phenoxy, methoxymethyl, methylthiomethyl, 1,3-oxazolyl, methoxymethoxy, hydroxyl, amino, tosyl, methylsulfanyl, trimethylsiloxy, dimethylamino, sulphate, nitro, halogens or the like.

12. A continuous process according to claim 10, wherein the polarising substituent bound to a ring atom of the aromatic ring structure adjacent to the ring atom bound to $P^1$ or $P^2$ is a fluorine atom.

13. A continuous process according to claim 1, wherein at least one of $R^1$ to $R^4$ is an aromatic moiety of which a ring atom of the aromatic ring structure is bound to either $P^1$ or $P^2$ and which has a non-polar substituent bound to a ring atom of the aromatic ring structure adjacent to the ring atom bound to $P^1$ or $P^2$.

14. A continuous process according to claim 13, wherein the non-polar substituent bound to a ring atom of the aromatic ring structure adjacent to the ring atom bound to $P^1$ or $P^2$ includes an alkyl or cycloalkyl group.

15. A continuous process according to claim 1, wherein X is —N($R^9$)—, where $R^9$ is a hydrocarbyl group, a heterohydrocarbyl group or an organoheteryl group.

16. A process according to claim 1, wherein the average activity of the activated catalyst is greater than 700 000 g/gCr/h at 100° C., 45 bar.

17. A process according to claim 1, wherein at least 35 mass % 1-octene is produced.

18. A process according to claim 1, wherein at least 45 mass % 1-octene is produced.

* * * * *